(12) United States Patent
Liu et al.

(10) Patent No.: US 7,943,658 B2
(45) Date of Patent: May 17, 2011

(54) INDOLE INDANE AMIDE COMPOUNDS USEFUL AS CB2 AGONISTS AND METHOD

(75) Inventors: Chunjian Liu, Pennington, NJ (US); Stephen T. Wrobleski, Whitehouse Station, NJ (US); Katerina Leftheris, Skillman, NJ (US); Gang Wu, Princeton, NJ (US); Philip M. Sher, Plainsboro, NJ (US); Bruce A. Ellsworth, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 375 days.

(21) Appl. No.: 12/177,319

(22) Filed: Jul. 22, 2008

(65) Prior Publication Data

US 2009/0041722 A1 Feb. 12, 2009

Related U.S. Application Data

(60) Provisional application No. 60/951,275, filed on Jul. 23, 2007.

(51) Int. Cl.
*A61K 31/404* (2006.01)
*C07D 209/04* (2006.01)
(52) U.S. Cl. .......... 514/419; 548/469; 548/492; 514/415
(58) Field of Classification Search .............. 548/469, 548/492; 514/415, 419
See application file for complete search history.

(56) References Cited

U.S. PATENT DOCUMENTS

| | | | |
|---|---|---|---|
| 5,401,758 A | 3/1995 | Atwal et al. | |
| 5,449,686 A | 9/1995 | Christensen, IV et al. | |
| 5,466,823 A | 11/1995 | Talley et al. | |
| 5,474,995 A | 12/1995 | Ducharme et al. | |
| 5,552,438 A | 9/1996 | Christensen, IV | |
| 5,633,272 A | 5/1997 | Talley et al. | |
| 5,998,428 A | 12/1999 | Barnette et al. | |
| 6,013,648 A | 1/2000 | Rinaldi et al. | |
| 6,291,523 B1 | 9/2001 | Fujimoto et al. | |
| 6,310,099 B1 | 10/2001 | Fujimoto et al. | |
| 6,716,987 B1 | 4/2004 | Ohshima et al. | |
| 7,115,646 B2 * | 10/2006 | Qiao ........................ | 514/397 |
| 2005/0119234 A1 | 6/2005 | Makriyannis et al. | |

FOREIGN PATENT DOCUMENTS

| | | |
|---|---|---|
| WO | WO96/25405 | 8/1996 |
| WO | WO97/14691 | 4/1997 |
| WO | WO97/38986 | 10/1997 |
| WO | WO98/03484 | 1/1998 |
| WO | WO99/12930 | 3/1999 |
| WO | WO99/47505 | 9/1999 |
| WO | WO00/26216 | 5/2000 |
| WO | WO00/52008 | 9/2000 |
| WO | WO01/13953 | 3/2001 |
| WO | WO01/58881 | 8/2001 |
| WO | WO02/18374 | 3/2002 |
| WO | WO2006/082400 | 8/2006 |
| WO | WO2006/100208 | 9/2006 |

OTHER PUBLICATIONS

Bundgaard, H., Design of Produgs, TOC, 1985.
Bundgaard, H., Design and Application of Prodrugs, A Textbook of Drug Design and Development, Chapter 5, pp. 113-191 (1991).
Bundgaard, H., Advanced Drug Delivery Reviews, 8, pp. 1-38 (1992).
Fuji, K. et al., "Novel Phosphodiesterase 4 Inhibitor T-440 Reverses and Prevents Human Bronchial Contraction Induced by Allergen", J. Pharmacal. Exp. Ther., 1998, 284(1):162.
Larock, R.C., Comprehensive Organic Transformations. A Guide to Functional Group Preparation, pp. 385-439 (1989).
Widder, K.J., Methods in Enzymology, Drug and Enzyme Targeting, vol. 112, pp. 309-396 (1985).

* cited by examiner

*Primary Examiner* — Golam M Shameem
(74) *Attorney, Agent, or Firm* — Ying Wang; Maureen S. Gibbons; Burton Rodney

(57) ABSTRACT

Indole indane amides which are CB2 agonists are provided which have the structure

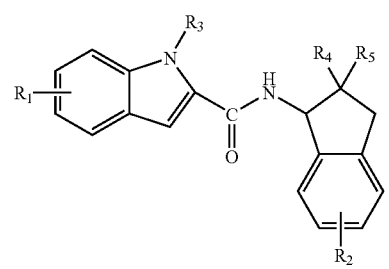

I wherein $R_1$, $R_2$, $R_3$, $R_4$ and $R_5$ are as defined herein, which compounds are useful in treating autoimmune diseases, inflammation, pain, cardiovascular disorders and other diseases mediated by CB2 receptors. A method for preventing or treating such diseases employing the compounds of the invention is also provided.

14 Claims, No Drawings

INDOLE INDANE AMIDE COMPOUNDS USEFUL AS CB2 AGONISTS AND METHOD

FIELD OF THE INVENTION

The present invention relates to indole indane amide compounds which are agonists of cannabinoid CB2 receptors and thus are useful in treating autoimmune diseases and related disorders, inflammation, pain, cardiovascular disorders and other diseases as disclosed hereinafter, and to a method for treating such diseases.

BACKGROUND OF THE INVENTION

Cannabinoid receptors are classified predominantly into two groups, a) central receptors (CB1) which are located mainly in the brain in neural cells and whose effects are principally associated with the central nervous system; and b) peripheral receptors (CB2) which are found in the spleen and are believed to have peripheral effects related to inflammation, autoimmune disorders and bronchial constriction.

BRIEF DESCRIPTION OF THE INVENTION

In accordance with the present invention, indole indane amide compounds are provided which have the formula

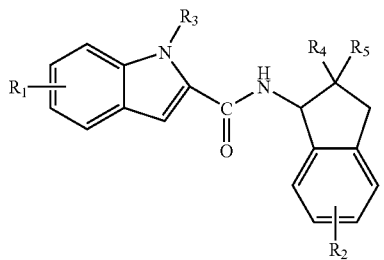

I its enantiomers and diastereomers, or a pharmaceutically acceptable salt thereof, a prodrug thereof, or a solvate thereof, wherein $R_1$ and $R_2$ are the same or different and are independently selected from a) hydrogen, hydroxyl, halogen, alkyl, alkoxy, alkoxyalkyl, cycloalkyl, aryloxy, nitro and cyano;

b) an amino group, an amido group, carboxyl, alkoxycarbonyl and a urea group; and c) aryl, heteroaryl, and heterocyclo;

$R_3$ is hydrogen or alkyl; and $R_4$ and $R_5$ are the same or different and are independently selected from hydrogen and alkyl.

In the above formula I compounds, the $R_1$ and/or $R_2$ amino group has the structure —$NR_6R_7$;

the $R_1$ and/or $R_2$ amido group has the structure

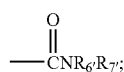

and the $R_1$ and/or $R_2$ urea group has the structure

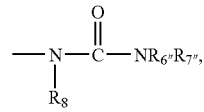

wherein $R_6$, $R_7$, and $R_6'$, $R_7'$, and $R_6''$ and $R_7''$ are the same or different and are independently selected from hydrogen, alkyl, cycloalkyl, alkoxyalkyl, heteroaryl, and heterocyclo; and $R_8$ is hydrogen or alkyl.

In preferred embodiments of the compounds of formula I of the invention $R_1$ is hydroxyl, halogen, hydrogen, nitro, amino or alkoxyalkylamino, more preferably, $R_1$ is hydroxyl, chloro, hydrogen, fluoro, nitro, amino or methoxyethylamino;

$R_2$ is cyano or alkoxycarbonyl;

more preferably, $R_2$ is cyano or methoxycarbonyl;

and still more preferably, $R_2$ is cyano;

$R_3$ is hydrogen, alkyl, dialkylaminoalkyl or heterocycloalkyl; more preferably, $R_3$ is hydrogen, methyl, dimethylaminoethyl or morpholinylethyl; and $R_4$ and $R_5$ are the same or different and are independently selected from alkyl; and more preferably, $R_4$ and $R_5$ are each methyl.

In still more preferred embodiments of the compounds of formula I $R_1$ is hydroxyl, halogen, hydrogen, nitro, amino or alkoxyalkylamino;

$R_2$ is cyano or alkoxycarbonyl;

$R_3$ is hydrogen, alkyl or heterocycloalkyl; and $R_4$ and $R_5$ are the same or different and are alkyl.

Still more preferred are compounds of formula I wherein $R_1$ is hydroxyl, chloro, hydrogen, fluoro, nitro, amino or methoxyethylamino;

$R_2$ is cyano or methoxycarbonyl;

$R_3$ is hydrogen, methyl or morpholinylethyl; and $R_4$ and $R_5$ are each methyl.

The invention further pertains to pharmaceutical compositions containing compounds of formula I, and to methods of treating conditions associated with the CB2 receptor, which methods include the step of administering to a mammal, including a human, dog, cat, horse, sheep or cow in need of treatment a pharmaceutically-acceptable amount of a compound of formula I.

In addition, in accordance with the present invention, a method is provided for preventing, inhibiting onset of, alleviating or treating a disease or disorder that is mediated by peripheral cannabinoid receptors CB2 which includes the step of administering to a mammal in need of treatment a therapeutically effective amount of a pharmaceutical composition containing a compound of formula I, a prodrug thereof, or a pharmaceutically acceptable salt thereof, solvate or stereoisomer thereof, wherein the disease or disorder to be treated is an inflammatory disease, an autoimmune disease, a respiratory disease, a cardiovascular disorder, a cerebralvascular disorder or tumors expressing CB2 receptors.

In another aspect of the present invention, a method is provided for treating cutaneous T cell lymphoma, rheumatoid arthritis, systemic lupus erythematosus, multiple sclerosis, glaucoma, diabetes (Type I), sepsis, shock, sarcoidosis, idiopathic pulmonary fibrosis, bronchopulmonary dysplasia, retinal disease, scleroderma, osteoporosis, renal ischemia, hypertension, myocardial infarction, arrhythmias, cerebral stroke, cerebral ischemia, nephritis, hepatitis, glomerulonephritis, Parkinson's disease, Sjögren's syndrome, pain, migraine, cluster headache, peripheral, viscerla, neuropathic, inflammatory and referred pain, cryptogenic fibrosing alveolitis, psoriasis, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD), bronchitis, colitis, coronary artery disease, melanoma, transplant rejection, graft versus host disease, Hashimoto's thyroiditis, Graves' disease, myasthenia gravis or Goodpasture's syndrome, which includes the step of administering to a mammal (including a human, dog, cat, horse, sheep or cow) in need of such treatment a therapeutically effective amount of a compound, a prodrug thereof, or a pharmaceutically acceptable salt, solvate or stereoisomer of the compound of formula I or a pharmaceutical composition containing such compound.

DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" or "lower alkyl" refers to straight or branched chain hydrocarbon groups of 1 to 20 carbon atoms, preferably 1 to 7 carbon atoms. The expression "lower alkyl" refers to unsubstituted or substituted alkyl groups of 1 to 4 carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms.

The alkyl group may be optionally substituted by one to four substituents selected from halogen, hydroxy, alkoxy, keto (=O), alkanoyl, aryloxy, alkanoyloxy, $NR_aR_b$, alkanoylamino, aroylamino, aralkanoylamino, alkanoylamino, arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, —$SO_2NR_aR_b$, nitro, cyano, —$CO_2H$, —$CONR_aR_b$, alkoxycarbonyl, aryl, guanidino and heteroaryls or heterocyclos (such as indolyl, imidazolyl, furyl, thienyl, thiazolyl, pyrrolidyl, pyridyl, pyrimidyl and the like), wherein $R_a$ and $R_b$ are selected from hydrogen, alkyl, aryl, aralkyl, cycloalkyl, cycloalkylalkyl, heteroaryl, heteroarylalkyl, heterocyclo, and heterocycloalkyl. The substituent on the alkyl optionally in turn may be further substituted, in which case it will be with substituted one or more of $C_{1-4}$alkyl, $C_{2-4}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenyloxy, and/or benzyloxy.

The term "alkenyl" refers to straight or branched chain substituted or unsubstituted hydrocarbon groups of 2 to 20 carbon atoms, preferably 2 to 15 carbon atoms, and most preferably 2 to 8 carbon atoms, having at least one double bond, and depending on the number of carbon atoms, up to four double bonds.

The alkenyl group may be optionally substituted by one to two substituents selected from those recited above for substituted alkyl groups.

The term "alkynyl" refers to straight or branched chain substituted or unsubstituted hydrocarbon groups of 2 to 20 carbon atoms, preferably 2 to 15 carbon atoms, and most preferably 2 to 8 carbon atoms, having at least one triple bond, and depending on the number of carbon atoms, up to four triple bonds.

The alkynyl group may be optionally substituted by one to two substituents selected from those recited above for alkyl groups.

When the term alkyl is used in connection with another group, as in heterocycloalkyl or cycloalkylalkyl, this means the identified (first named) group is bonded directly through an alkyl group which may be branched or straight chain (e.g., cyclopropyl$C_{1-4}$alkyl means a cyclopropyl group bonded through a straight or branched chain alkyl group having one to four carbon atoms.). In the case of substituents, as in a substituted cycloalkylalkyl, or a substituted alkanoyl or other group which includes an alkyl as part thereof, the alkyl portion of the group, besides being branched or straight chain, may be substituted as recited above for substituted alkyl groups and/or the first named group (e.g., cycloalkyl) may be substituted as recited herein for that group.

The term "halogen" or "halo" refers to fluorine, chlorine, bromine and iodine.

The term "aryl" refers to monocyclic or bicyclic aromatic substituted or unsubstituted hydrocarbon groups having 6 to 12 carbon atoms in the ring portion, such as phenyl, naphthyl, and biphenyl groups. Aryl groups may optionally include one to three additional rings (either cycloalkyl, heterocyclo or heteroaryl) fused thereto.

Examples include:

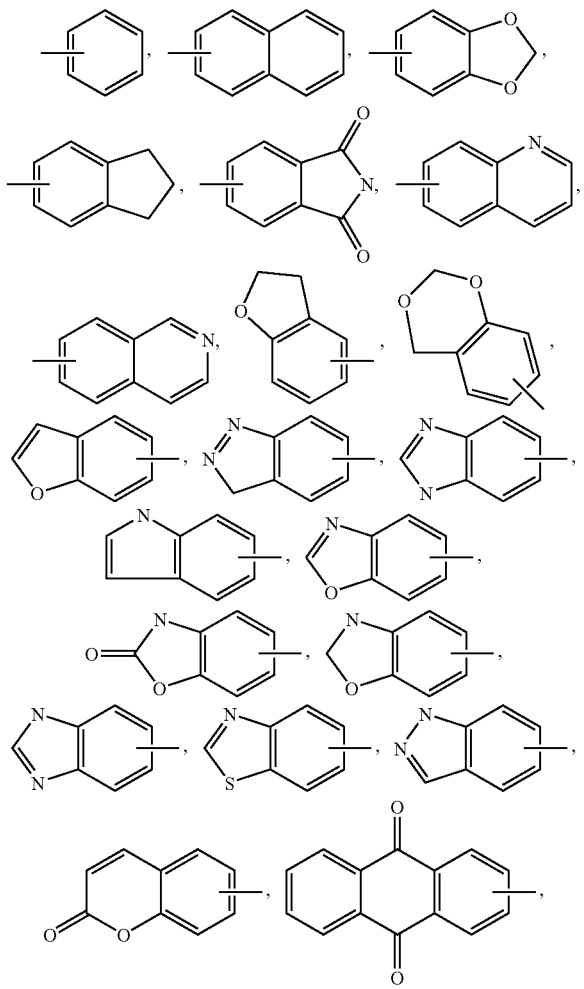

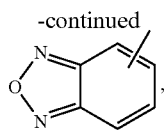

and the like. Each ring of the aryl may be optionally substituted with one to three $R_c$ groups, wherein $R_c$ at each occurrence is selected from alkyl, substituted alkyl, halogen, trifluoromethoxy, trifluoromethyl, —SR, —OR, —NRR', —NRSO$_2$R', —SO$_2$R, —SO$_2$NRR', —CO$_2$R', —C(=O)R', —C(=O)NRR', —OC(=O)R', —OC(=O)NRR', —NRC(=O)R', —NRCO$_2$R', phenyl, $C_{3-7}$ cycloalkyl, and five-to-six membered heterocyclo or heteroaryl, wherein each R and R' is selected from hydrogen, alkyl, substituted alkyl, alkenyl, substituted alkenyl, phenyl, $C_{3-7}$cycloalkyl, and five-to-six membered heterocyclo or heteroaryl, except in the case of a sulfonyl group, then R is not going to be hydrogen. Each substituent $R_c$ optionally in turn may be further substituted by one or more (preferably 0 to 2) $R_d$ groups, wherein $R_d$ is selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenylethyl, phenyloxy, and benzyloxy.

The term "aralkyl" refers to an aryl group bonded directly through an alkyl group, such as benzyl, wherein the alkyl group may be branched or straight chain. In the case of a substituted aralkyl group, the alkyl portion of the group besides being branched or straight chain, may be substituted as recited above for substituted alkyl groups and/or the aryl portion may be substituted as recited herein for aryl. Thus, the term "optionally substituted benzyl" refers to the group

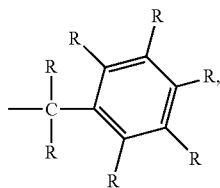

wherein each R group may be hydrogen or may also be selected from $R_c$ as defined above, in turn optionally substituted with one or more $R_d$. At least two of these "R" groups should be hydrogen and preferably at least five of the "R" groups is hydrogen. A preferred benzyl group involves the alkyl-portion being branched to define

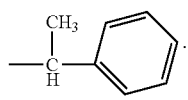

The term "heteroaryl" refers to a substituted or unsubstituted aromatic group for example, which is a 4 to 7 membered monocyclic, 7 to 11 membered bicyclic, or 10 to 15 membered tricyclic ring system, which has at least one heteroatom and at least one carbon atom-containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. It may optionally be substituted with one to three (preferably 0 to 2) $R_c$ groups, as defined above for aryl, which in turn may be substituted with one or more (preferably o to 2) $R_d$ groups, also as recited above.

Exemplary monocyclic heteroaryl groups include pyrrolyl, pyrazinyl, pyrazolinyl, imidazolyl, oxazolyl, isoxazolyl, thiazolyl (i.e., (i.e., 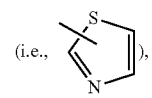), thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "cycloalkyl" refers to a saturated or partially unsaturated non-aromatic cyclic hydrocarbon ring system, preferably containing 1 to 3 rings and 3 to 7 carbon atoms per ring, which may be substituted or unsubstituted and/or which may be fused with a $C_3$-$C_7$ carbocyclic ring, a heterocyclic ring, or which may have a bridge of 3 to 4 carbon atoms. The cycloalkyl groups including any available carbon or nitrogen atoms on any fused or bridged rings optionally may have 0 to 3 (preferably 0-2) substituents selected from $R_c$ groups, as recited above, and/or from keto (where appropriate) which in turn may be substituted with one to three $R_d$ groups, also as recited above. Thus, when it is stated that a carbon-carbon bridge may be optionally substituted, it is meant that the carbon atoms in the bridged ring optionally may be substituted with an $R_c$ group, which preferably is selected from $C_{1-4}$alkyl, $C_{2-4}$alkenyl, halogen, haloalkyl, haloalkoxy, cyano, amino, $C_{1-4}$alkylamino, amino$C_{1-4}$alkyl, hydroxy, hydroxy$C_{1-4}$alkyl, and $C_{1-4}$alkoxy. Exemplary cycloalkyl groups include cyclopropyl, cyclobutyl, cyclopentyl, cyclohexyl, cycloheptyl, bicycloheptane, cyclooctyl, cyclodecyl, cyclododecyl, and adamantyl.

The terms "heterocycle", "heterocyclic" and "heterocyclo" each refer to a fully saturated or partially unsaturated nonaromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quaternized. Preferably two adjacent heteroatoms are not simultaneously selected from oxygen and nitrogen. The heterocyclic group may be attached at any nitrogen or carbon atom. The heterocyclo groups optionally may have 0 to 3 (preferably 0-2) substituents selected from keto (=O), and/or one or more $R_c$ groups, as recited above, which in turn may be substituted with one to three $R_d$ groups, also as recited above.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Also included are smaller heterocyclos, such as epoxides and aziridines.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., indolyl), the reference is intended to include rings having 0 to 3, preferably 0-2, substituents selected from those recited above for the aryl, cycloalkyl, heterocyclo and/or heteroaryl groups, as appropriate. Additionally, when reference is made to a specific heteroaryl or heterocyclo group, the reference is intended to include those systems having the maximum number of non-cumulative double bonds or less than the maximum number of double bonds. Thus, for example, the term "isoquinoline" refers to isoquinoline and tetrahydroisoquinoline.

Additionally, it should be understood that one skilled in the field may make appropriate selections for the substituents for the aryl, cycloalkyl, heterocyclo, and heteroaryl groups to provide stable compounds and compounds useful as pharmaceutically-acceptable compounds and/or intermediate compounds useful in making pharmaceutically-acceptable compounds.

The term "heteroatoms" shall include oxygen, sulfur and nitrogen.

The term "haloalkyl" means an alkyl having one or more halo substituents.

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with a substituted alkyl, a substituted alkenyl, aryl, cycloalkyl, and so forth, are as follows: alkoxy is —$OR^e$, alkanoyl is —$C(=O)R^e$, aryloxy is —OAr, alkanoyloxy is —$OC(=O)R^e$, amino is —$NH_2$, alkylamino is —$NHR^e$ or —$N(R^e)_2$, arylamino is —NHAr or —$NR^eAr$, aralkylamino is —NH—$R^f$—Ar, alkanoylamino is —NH—$C(=O)R^e$, aroylamino is —NH—$C(=O)Ar$, aralkanoylamino is —NH—$C(=O)R^f$—Ar, thiol is —SH, alkylthio is —$SR^e$, arylthio is —SAr, aralkylthio is —S—$R^f$—Ar, alkylthiono is —$S(=O)R^e$, arylthiono is —$S(=O)Ar$, aralkylthiono is —$S(=O)R^f$—Ar, alkylsulfonyl is —$SO_{(q)}R^e$, arylsulfonyl is —$SO_{(q)}Ar$, arylsulfonylamine is —$NHSO_{(q)}Ar$, alkylsulfonylamine is —$NHSO_2R^e$, aralkylsulfonyl is —$SO_{(q)}R^fAr$, sulfonamido is —$SO_2NH_2$, substituted sulfonamide is —$SO_2NHR^e$ or —$SO_2N(R^e)_2$, nitro is —$NO_2$, carboxy is —$CO_2H$, carbamyl is —$CONH_2$, substituted carbamyl is —$C(=O)NHR^g$ or —$C(=O)NR^gR^h$, alkoxycarbonyl is —$C(=O)OR^e$, carboxyalkyl is —$R^f$—$CO_2H$, sulfonic acid is —$SO_3H$, guanidino is

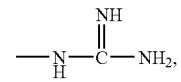

and ureido is

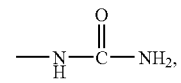

wherein $R^e$ is alkyl or substituted alkyl as defined above, $R^f$ is alkylene or substituted alkylene as defined above, $R^g$ and $R^h$ are selected from alkyl, substituted alkyl, aryl, aralkyl, cycloalkyl, heterocyclo, and heteroaryl; Ar is an aryl as defined above, and q is 2 or 3.

Throughout the specification, groups and substituents thereof may be chosen by one skilled in the field to provide stable moieties and compounds.

The compounds of the present invention may form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of the present invention may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds of the present invention may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the present invention may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, pp. 1-38 (1992), each of which is incorporated herein by reference.

It should further be understood that solvates (e.g., hydrates) of the compounds of Formula (I) are also with the scope of the present invention. Methods of solvation are generally known in the art.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein and are within the scope of the formula I compounds of the invention. Such compounds have a variety of potential uses, e.g., as standards and reagents in determining the ability of a potential pharmaceutical to bind to target proteins or receptors, or for imaging compounds of this invention bound to biological receptors in vivo or in vitro.

ABBREVIATIONS

For ease of reference, the following abbreviations are employed herein, including the methods of preparation and Examples that follow:

| | |
|---|---|
| MeOH = | methanol |
| EtOH = | ethanol |
| EtOAc = | ethyl acetate |
| Boc = | tert-butyloxycarbonyl |
| BOP = | Benzotriazole-1-yl-oxy-tris-(dimethylamino)-phosphonium-hexafluorophosphate |
| CBZ = | carbobenzyloxy or carbobenzoxy or benzyloxycarbonyl |
| DBU = | 1,8-diazabicyclo[5.4.0] undec-7-ene |
| DCM = | dichloromethane |
| DMF = | dimethyl formamide |
| DMSO = | dimethyl sulfoxide |
| DPPA = | diphenyl phosphoryl azide |
| TFA = | trifluoroacetic acid |
| THF = | tetrahydrofuran |
| p-TsOH = | para-toluenesulphonic acid |
| HATU = | O-(7-Azabenzotriazol-1-yl-N,N,N',N'-tetramethyluronim hexafluorophosphate |
| EDC or EDCI, or EDAC = | 1-(3-Dimethylaminopropyl)-3-ethylcarbodiimide hydrochloride |
| DIPEA = | diisopropylethylamine |
| HOBt = | 1-hydroxybenzotriazole hydrate |
| m-CPBA = | m-chloroperbenzoic acid |
| NMP = | N-methylpyrrolidinone |
| Pd/C = | palladium on carbon |
| sec = | second (s) |
| min = | minute(s) |
| h = | hour(s) |
| L = | liter |
| mL = | milliliter |
| μL = | microliter |
| g = | gram(s) |
| mg = | milligram(s) |
| mol = | moles |
| mmol = | millimole(s) |
| N = | Normal |
| M = | Molar |
| ° C. = | degrees Celsius |
| rt = | room temperature |
| Ret. time or $t_R$ = | retention time (minutes) |
| anhyd. = | anhydrous |
| sat or sat'd = | saturated |
| aq. = | aqueous |
| HPLC = | high performance liquid chromatography |
| LCMS = | high performance liquid chromatography/mass spectrometry |
| MS = | mass spectrometry |
| NMR = | nuclear magnetic resonance |
| MHz = | megahertz |
| s = | singlet |
| m = | multiplet |
| d = | doublet |
| dd = | doublet of doublet |

Methods of Preparation

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s). All documents cited are incorporated herein by reference in their entirety.

Compounds of the present invention can be made by many methods, which will be known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. The preparation of heterocycles useful to this invention are described in the series of books: Katritzky, A. R. et al., eds., *Comprehensive Heterocyclic Chemistry. The Structure, Reactions, Synthesis and Uses, of Heterocyclic Compounds*, Pergamon Press, New York, First Edition (1984), and Katritzky, A. R. et al., eds., "*Comprehensive Heterocyclic Chemistry II. A Review of the Literature 1982-1995. The Structure, Reactions, Synthesis and Uses, of Heterocyclic Compounds*", Pergamon Press, New York (1996).

Acids or acid chlorides, used for the preparation of compounds useful to this invention may be commercially available or readily prepared by many methods known to one skilled in the art of organic chemistry, and are described in Richard C. Larock, *Comprehensive Organic Transformations. A Guide to Functional Group Preparation*, pp. 385-439, VCH Publishers, Inc. (1989).

General methods for the synthesis of compounds useful for this invention are outlined in the following schemes.

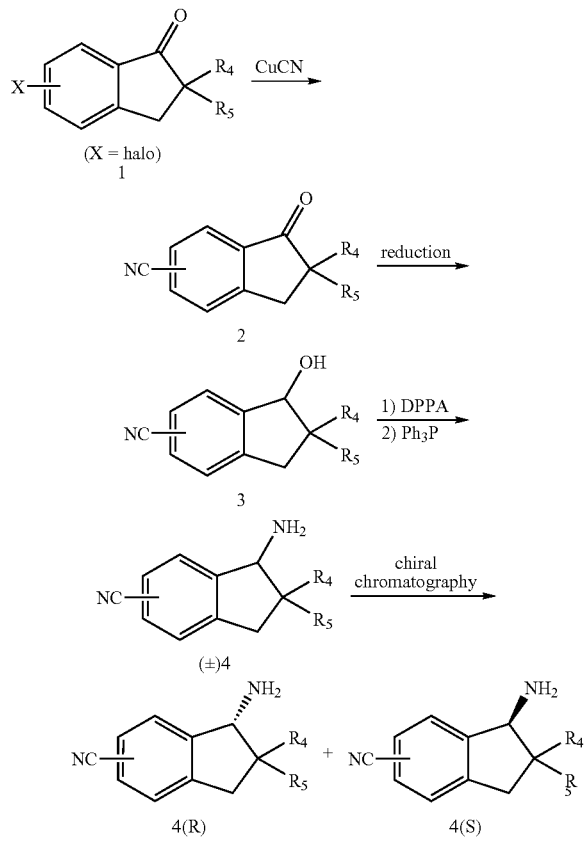

Compound 1 can be prepared according to U.S. Pat. No. 5,401,758. As depicted in Scheme 1, compound 2 is prepared from compound 1 by reacting with a cyanide reagent, such as copper cyanide, in a suitable solvent such as NMP. Reduction of 2 in the presence of a suitable reducing agent such as NaBH$_4$ in a suitable solvent such as ethanol affords alcohol 3. Conversion of alcohol 3 to amine 4 is undertaken by reaction of 3 with DPPA in the presence of a suitable base such as DBU in a solvent such as toluene followed by reduction of the intermediate azide with a reducing reagent such as PPh$_3$ in a solvent such as acetonitrile. Finally, the racemic amine 4 can be resolved by chiral HPLC methods to afford the optically pure enantiomers 4R and 4S.

It will be appreciated that the R$_1$ CN moiety in compounds 2 to 4 may be replaced with any of the R$_1$ moieties included in the definition of R$_1$ and such compounds may be prepared employing procedures as disclosed in U.S. Pat. No. 5,401,758.

As illustrated in Scheme 2, amine 4 (which can be prepared as shown in Scheme 1) is coupled to acid 5 to afford amide 6 using conventional methods known in the art for amide bond formations. Furthermore, amide 6 can be alkylated with alkylating agents R$_3$—X wherein X is a halide, such as Cl or Br, in the presence of a suitable base such as NaH in a suitable solvent such as DMF to afford compounds of formula I of the invention.

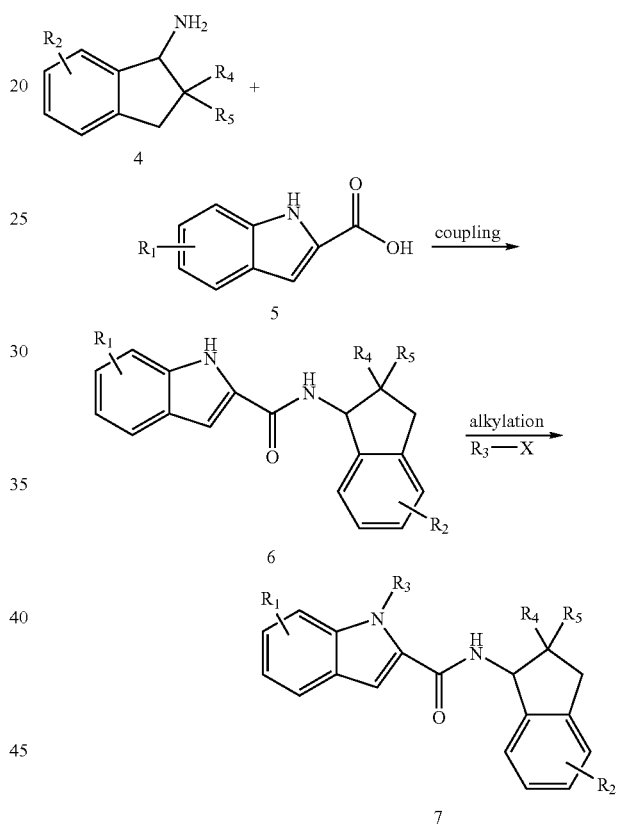

The compounds of formula I of the invention may be prepared in crystalline or non-crystalline form, and, if crystalline, may optionally be hydrated or solvated. This invention includes within its scope stoichiometric hydrates or solvates as well as compounds containing variable amounts of water and/or solvent.

Utility

The compounds of formula I of the invention bind selectively to the CB2 receptor, and are therefore useful in treating CB2 receptor mediated diseases such as autoimmune diseases, pain, inflammation and cardiovascular disorders including rheumatoid arthritis, systemic lupus erythematosus, multiple sclerosis, glaucoma, diabetes, osteoporosis, renal ischemia, cerebral stroke, cerebral ischemia, nephritis, psoriasis, allergy, inflammatory disorders of the lungs and gastrointestinal tract such as Crohn's disease, and respiratory tract disorders such as reversible airway obstruction, asthma, chronic obstructive pulmonary disease (COPD) and bronchitis and other diseases and disorders as set out hereinafter. This utility is manifested as demonstrated by activity in the following assay.

CB2 agonists of formula I of the invention have anti-inflammatory and/or immunomodulatory activity and are useful in the treatment of various medical conditions including, e.g., cutaneous T cell lymphoma, systemic lupus erythematosus, multiple sclerosis, glaucoma, diabetes, osteoporosis, renal ischemia, myocardial infarction, cerebral stroke, cerebral ischemia, nephritis, hepatitis, glomerulonephritis, cryptogenic fibrosing aveolitis, psoriasis, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis, in the treatment of inflammation, for example in the treatment of skin conditions such as sunburn, burns, eczema, dermatitis, psoriasis; ophthalmic diseases such as glaucoma, retinitis, retinopathies, uveitis and of acute injury to the eye tissue such as conjunctivitis; lung disorders such as asthma, bronchitis, emphysema, allergic rhinitis, pigeon fancier's disease, farmer's lung; gastrointestinal tract disorders such as aphthous ulcer, atopic gastritis, gastritis varialoforme, ulcerative colitis, coeliac disease, regional ileitis, irritable bowel syndrome, gastrointestinal reflux disease; organ transplantation; other conditions with an inflammatory component such as vascular disease, migraine, periarteritis nodosa, thyroiditis, aplastic anemia, Hodgkin's disease, sclerodoma, myaesthenia gravis, sarcoidosis, nephrotic syndrome, Bechet's syndrome, polymyositis, gingivitis, myocardial ischemia, pyrexia, tendonitis, bursitis, and Sjögren's syndrome.

The compounds of formula I are also useful as analgesics, and as such are useful in the treatment of chronic inflammatory pain, including pain associated with rheumatoid arthritis, osteoarthritis, rheumatoid spondylitis, gouty arthritis and juvenile arthritis, including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of formula I of the invention may also be useful in disease modification or joint structure preservation in multiple sclerosis, rheumatoid arthritis, osteoarthritis, rheumatoid spondylitis, gouty arthritis and juvenile arthritis.

The compounds of formula I are useful in the treatment of neuropathic pain. Neuropathic pain syndromes can develop following neuronal injury, for example in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions.

The compounds of formula I may also be useful in the treatment of fever.

The compounds of formula I may also be useful in the treatment of bladder hyperrelexia following bladder inflammation.

The compounds of formula I may also be effective in increasing the latency of HIV infection.

The compounds of formula I may also be useful in the treatment of diseases of abnormal platelet function such as occlusive vascular diseases; in the treatment of neuritis, heart; burn, dysphagia, pelvic hypersensitivity, urinary incontinence, cystitis or incontinence; for the preparation of a drug with diuretic action; in the treatment of impotence or erectile dysfunction; for attenuating the hemodynamic side effects of non-steroidal anti-inflammatory drugs (NSAID's) and cyclooxygenase-2 (COX-2) inhibitors.

The compounds of formula I may also be useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, motor neuron disease); vascular dementia (including multi-infarct dementia); as well as dementia associated with intracranial space occupying lesions; trauma; infections and related conditions (including HIV infection); dementia in Parkinson's disease, metabolism; toxins; anoxia and vitamin deficiency; and mild cognitive impairment associated with ageing, particularly Age Associated Memory Impairment. The compounds may also be useful for the treatment of amyotrophic lateral sclerosis (ALS) and neuroinflammation.

The compounds of formula I may also be useful in neuroprotection and in the treatment of neurodegeneration following stroke, cardiac arrest, pulmonary bypass, traumatic brain injury, spinal cord injury or the like; in the treatment of tinnitus; in the treatment of psychiatric disease for example schizophrenia, depression (which term is used herein to include bipolar depression, unipolar depression, single or recurrent major depressive episodes with or without psychotic features, catatonic features, melancholic features, atypical features or postpartum onset, seasonal affective disorder, dysthymic disorders with early or late onset and with or without atypical features, neurotic depression and social phobia, depression accompanying dementia for example of the Alzheimer's type, schizoaffective disorder or the depressed type, anxiety disorders including generalized anxiety disorder and social anxiety disorder, panic disorder, agoraphobia, social phobia, obsessive compulsive disorder and post-traumatic stress disorder, memory disorders, including dementia, amnesic disorders and age-associated memory impairment, disorders of eating behaviors, including anorexia nervosa and bulimia nervosa, sexual dysfunction, sleep disorders including disturbances of circadian rhythm, dyssomnia, insomnia, sleep apnea and narcolepsy, withdrawal from abuse of drugs such as of cocaine, ethanol, nicotine, benzodiazopines, alcohol, caffeine, phencyclidine (phencyclidine-like compounds), opiates such as cannabis, heroin, morphine, amphetamine or amphetamine-related drugs such as dextroamphetamine, methylamphetamine or a combination thereof.

The compounds of formula I may also be useful in preventing or reducing dependence on, or preventing or reducing tolerance or reverse tolerance to, a dependence inducing agent. Examples of dependence-inducing agents include opioids such as morphine, CNS depressants such as ethanol, psychostimulants such as cocaine and nicotine.

The compounds of formula I may also be useful in the treatment of kidney dysfunction (nephritis, particularly mesangial proliferative glomerulonephritis, nephritic syndrome), liver dysfunction (hepatitis, cirrhosis), gastrointestinal dysfunction (diarrhea) and colon cancer.

It is to be understood that references to treatment includes both treatment of established symptoms and prophylactic treatment unless explicitly stated otherwise.

According to a further aspect of the invention, a method of treating a mammal including a human suffering from a condition which is mediated by the activity of cannabinoid 2 receptors as provided which includes the step of administering to mammal or patient in need of treatment a therapeutically effective amount of a compound of formula I.

According to a further aspect of the invention, a method is provided of healing a mammal including a human suffering from an immune disorder, an inflammatory disorder, pain, rheumatoid arthritis, multiple sclerosis, osteoarthritis or osteoporosis which method includes the step of administering to the patient an effective amount of a compound of formula I.

The pain may for example be selected from inflammatory pain, visceral pain, cancer pain, neuropathic pain, lower back pain, muscular skeletal, post operative pain, acute pain and migraine. More particularly the inflammatory pain may be pain associated with rheumatoid arthritis or osteoarthritis.

According to one aspect of the invention, there is provided a compound of formula I for use as a medicament in the treatment I of pain.

According to another aspect of the invention, there is provided the use of a compound of formula I in the manufacture of a therapeutic agent for the treatment or prevention of a condition such an immune disorder, an inflammatory disorder, pain, rheumatoid arthritis, multiple sclerosis, osteoarthritis or osteoporosis.

The CB2 receptor compounds of formula I for use in the present invention may be used in combination with other therapeutic agents, for example COX-2 inhibitors, such as celecoxib, deracoxib, rofecoxib, valdecoxib, parecoxib or COX-189; 5-lipoxygenase inhibitors; NSAID's, such as aspirin, diclofenac, indomethacin, nabumetone or ibuprofen; leukotriene receptor antagonists; adenosine A1 receptor agonists; sodium channel blockers, such as lamotrigine; NMDA receptor modulators, such as glycine receptor antagonists; gabapentin and related compounds; tricyclic antidepressants such as amikiptyline; neurone stabilizing antiepileptic drugs; mono-aminergic uptake inhibitors such as venlafaxine; opioid analgesics; local anesthetics; $5HT_1$ agonists, such as kiptans, for example sumatriptan, naratriptan, zolmitriptan, eletriptan, frovatriptan, almotriptan or rizatriptan; $EP_1$ receptor ligands, $EP_4$ receptor ligands; $EP_2$ receptor ligands; $EP_3$ receptor ligands; $EP_4$ antagonists; $EP_2$ antagonists and $EP_3$ antagonists; bradykinin receptor ligands and vanilloid receptor ligand, antirheumatoid arthritis drugs, for example anti TNF drugs e.g., enbrel, remicade, anti-IL-1 drugs, or DMARDS e.g., leflunamide. When the compounds are used in combination with other therapeutic agents, the compounds may be administered either sequentially or simultaneously by any convenient route.

Additional COX-2 inhibitors are disclosed in U.S. Pat. Nos. 5,474,995, 5,633,272, 5,466,823, 6,310,099 and 6,291,523; and in WO 96/25405, WO 97/38986, WO 98/03484, WO 97/14691, WO 99/12930, WO 00/26216, WO 00/52008, WO 00/38311, WO 01/58881 and WO 02/18374.

Additionally, a compound of the present invention may be co-administered or used in combination with disease-modifying antirheumatic drugs (DMARDS) such as methotrexate, azathioptrine, leflunomide, pencillinamine, gold salts, mycophenolate mofetil, cyclophosphamide and other similar drugs. They may also be co-administered with or used in combination with NSAIDS such as piroxicam, naproxen, indomethacin, ibuprofen and the like; COX-2 selective inhibitors such as Vioxx and Celebrex®; COX-1 inhibitors such as Feldene; immunosuppressives such as steroids, cyclosporine, Tacrolimus, rapamycin and the like; biological response modifiers (BRMs) such as Enbrel, Remicade, IL-1 antagonists, anti-CD40, anti-CD28, IL-10, anti-adhesion molecules and the like; and other anti-inflammatory agents such as p38 kinase inhibitors, PDE4 inhibitors, TACE inhibitors, chemokine receptor antagonists, Thalidomide and other small molecule inhibitors of pro-inflammatory cytokine production. Other drugs that the compounds of the invention may be co-administered or used in combination with include Anaprox, Arava, Arthrotec, Azulfidine, Aspirin, Cataflam, Celestone Soluspan, Clinoril, Cortone Acetate, Cuprimine, Daypro, Decadron, Depen, Depo-Medrol, Disalcid, Dolobid, Naprosyn, Gengraf, Hydrocortone, Imuran, Indocin, Lodine, Motrin, Myochrysine, Nalfon, Naprelan, Neoral, Orudis, Oruvail, Pediapred, Plaquenil, Prelone, Relafen, Solu-Medrol, Tolectin, Trilisate and Volataren. These include any formulation of the above-named drugs.

For the treatment of multiple sclerosis, the compounds of formula I of the invention may be co-administered or used in combination with Avonex, Betaseron and Copaxone.

For combination treatment with more than one active agent, where the active agents are in separate dosage formulations, the active agents may be administered separately or in conjunction. In addition, the administration of one element may be prior to, concurrent to, or subsequent to the administration of the other agent.

Suitable 5HT3 antagonists which may be used in combination with the compounds of formula I of the invention include for example ondansetron, granisetron, metoclopramide.

Suitable serotonin agonists which may be used in combination with the compounds of formula I of the invention include sumatriptan, rauwolscine, yohimbine, metoclopramide.

Suitable SSRIs which may be used in combination with the compounds of formula I of the invention include fluoxetine, citalopram, femoxetine, fluvoxamine, paroxetine, indalpine, sertraline, zimeldine.

Suitable SNRIs which may be used in combination with the compounds of formula I of the invention include venlafaxine and reboxetine.

Suitable tricyclic antidepressants which may be used in combination with the compounds of formula I of the invention include imipramine, amitriptiline, chlomipramine and nortriptiline.

Suitable dopaminergic antidepressants which may be used in combination with the compounds of formula I of the invention include bupropion and amineptine.

Compounds of formula I of the invention may used in combination with PDE4 inhibitors. The PDE4 inhibitor useful in this invention may be any compound that is known to inhibit the PDE4 enzyme or which is discovered to act in as PDE4 inhibitor, and which is only or essentially only a PDE4 inhibitor, not compounds which inhibit to a degree of exhibiting a therapeutic effect other members of the PDE family as well as PDE4. There are at least two binding forms on human monocyte recombinant PDE4 (hPDE4) at which inhibitors bind. One explanation for these observations is that hPDE4 exists in two distinct forms. One binds the likes of rolipram and denbufylline with a high affinity while the other binds these compounds with a low affinity. The most suitable PDE4 inhibitors of for use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Generally it is most advantageous to use a PDE4 antagonists which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. Most suitable are those PDE4 inhibitors which have an $IC_{50}$ ratio of greater than 0.5, and particularly those compounds having a ratio of greater than 1.0. Reference is made to U.S. Pat. No. 5,998, 428, which describes these methods in more detail. It is incorporated herein in full as though set forth herein.

Compounds of formula I of the invention or combinations with PDE4 can be used in treating inflammation, lung disorders and as bronchodilators.

A further aspect of the invention is one or more compounds of formula I in combination with one or more PDE4 inhibitors or a pharmaceutical derivative thereof and pharmaceutical compositions comprising said combination.

A further aspect of the invention is a method of treating inflammation, lung disorders for example asthma, bronchitis, emphysema, allergic rhinitis, respiratory distress syndrome, pigeon fancier's disease, farmer's lung, chronic obstructive pulmonary disease, (COPD) and cough or a disorder which can be treated with a broncodilator which includes the step of administering to a mammal including a human in need of treatment, an effective amount of one or more compounds of formula I and an effective amount of one or more PDE4 inhibitors.

An additional aspect of the invention is the use of an effective amount of one or more compounds of formula I and an effective amount of one or more PDE4 inhibitors in the manufacture of a medicament in the treatment of inflammation or lung disorders for example asthma, bronchitis, emphysema, allergic rhinitis, respiratory distress syndrome, pigeon fancier's disease, farmer's lung, chronic obstructive pulmonary disease, (COPD) and cough, or for the manufacture of a bronchodilator.

As used herein cough can have a number of forms and includes productive, non-productive, hyperreactive, asthma and COPD associated.

A suitable patient pack may comprise an effective amount of one or more compounds of formula I and an effective amount of one or more PDE4 inhibitors or a pharmaceutical derivative thereof.

Suitable PDE4 compounds are cis [cyano-4-(3-cyclopentyloxy-4-methoxyphenyl)cyclohexan-1-carboxylate] also known as cilomilast or Ariflo™, 2-carbomethoxy-4-cyano-4-(3-cyclopropylmethoxy-4-difluoromethoxyphenyl)cyclohexan-1-one, and cis [4-cyano-4-(3-cyclopropylmethoxy-4-difluoromethoxyphenyl)cyclohexan-1-ol]. They can be made by the process described in U.S. Pat. Nos. 5,449,686 and 5,552,438. Other PDE4 inhibitors, specific inhibitors, which can be used in this invention are AWD-12-281 from ASTA MEDICA (Hofgen, N. et al., 15th EFMC Int. Symp. Med. Chem. (September 6-10, Edinburgh) 1998, Abst P.98); a 9-benzyladenine derivative nominated NCS-613 (INSEAM); D-4418 from Chiroscience and Schering-Plough; a benzodiazepine PDE4 inhibitor identified as CI-1018 (PD-168787; Parke-Davis/Warner Lambert); a benzodioxole derivative Kyowa Hakko disclosed in WO 99/16766; V-11294A from Napp (Landells, L. J. et al., Eur. Resp. J. [Annu. Cong. Eur. Resp. Soc. (September 19 23, Geneva) 1998], 1998, 12 (Suppl. 28): Abst P2393); roflumilast (CAS reference No. 162401-32-3) and a pthalazinone (WO 99/47505) from Byk-Gulden (now Altana); or a compound identified as T-440 (Tanabe Seiyaku; Fuji, K. et al., J. Pharmacol. Exp. Ther., 1998, 284(1):162).

Additional PDE4 inhibitors are disclosed on pages 2 to 15 of WO 01/13953. Specifically selected are arofylline, atizoram, BAY-19-8004, benafentrine, BYK-33043, CC-3052, CDP-840, cipamfylline, CP-220629, CP-293121, D-22888, D-4396, denbufylline, filaminast, GW-3600, ibudilast, KF-17625, KS-506-G, laprafylline, NA-0226A, NA-23063A, ORG-20241, ORG-30029, PDB-093, pentoxifylline, piclamilast, rolipram, RPR-117658, RPR-122818, RPR-132294, RPR-132703, RS-17597, RS-25344-000, SB-207499, SB-210667, SB-211572, SB-211600, SB-212066, SB-212179, SDZ-ISQ-844, SDZ-MNS-949, SKF-107806, SQ-20006, T-2585, tibenelast, tolafentrine, UCB-29646, V-11294A, YM-58997, YM-976 and zardaverine.

Suitably the PDE4 inhibitor is selected from cilomilast, AWD-12-281, NCS-613, D-4418, CI-1018, V-11294A, roflumilast or T-440.

The combinations referred to above may contain one or more compounds of formula I in combination with one or more additional therapeutic agents.

It will be appreciated that the compounds of any of the above combinations or compositions may be administered simultaneously (either in the same or different pharmaceutical formulations), separately or sequentially.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or: combined pharmaceutical formulations.

When a compound of formula I is used in combination with a second therapeutic agent active against the same disease state the dose of each compound may differ from that when the compound is used alone. Appropriate doses will be readily appreciated by those skilled in the art.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating CB2 receptor associated conditions as described above. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

EXAMPLES

The invention will now be further described by the following working examples, which are among preferred embodiments of the invention. These examples are illustrative rather than limiting. There may be other embodiments that fall within the spirit and scope of the invention as defined by the appended claims.

Example 1

(R)—N-(6-Cyano-2,2-dimethyl-2,3-dihydro-1H-inden-1-yl)-5-hydroxy-1H-indole-2-carboxamide

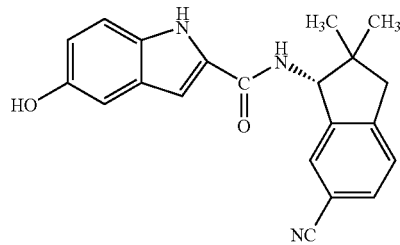

Step A: 2,2-Dimethyl-3-oxo-2,3-dihydro-1H-indene-5-carbonitrile

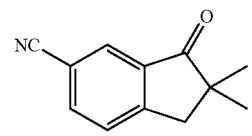

A slurry of 6-bromo-2,2-dimethyl-2,3-dihydro-1H-inden-1-one (U.S. Pat. No. 5,401,758) (24.97 g, 0.104 mol) and CuCN (18.7 g, 0.208 mol) in NMP (160 mL) was heated at 175° C. for 4 h. After cooling to rt, the reaction mixture was poured into EtOAc (300 mL) and water (200 mL) with stirring. After 15 min, the solid was collected and the filter cake was rinsed with EtOAc (150 mL). The resulting two layers were separated and the aqueous portion was extracted with EtOAc (150 mL×3). The combined organic layer was washed with brine, dried over magnesium sulfate, filtered and concentrated under reduced pressure to give a dark oil, which was divided into three portions and purified by flash chromatography on silica gel (120 g) eluting with EtOAc/Hexane mixtures to provide the title compound as a near colorless oil after concentration in vacuo (17.8 g, 90% yield). HPLC Ret. time: 2.55 min. LCMS MH+ (m/z) 186.31. ¹H NMR: (DMSO-d₆, 400 MHz): δ 8.13 (s, 1H), 8.11 (d, 1H), 7.78 (d, 1H), 3.10 (s, 2H), 1.15 (s, 6H).

Step B: 3-Hydroxy-2,2-dimethyl-2,3-dihydro-1H-indene-5-carbonitrile

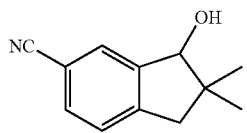

To a solution of Step A. 2,2-dimethyl-3-oxo-2,3-dihydro-1H-indene-5-carbonitrile (17.8 g, 0.096 mol) in ethanol at 0° C. was added NaBH₄ (7.27 g, 0.192 mol) as a solid and the resulting mixture was warmed to rt gradually and stirred for ~16 h. After cooling to 0° C., aq HCl (1N, 300 mL) was added slowly with vigorously stirring. After additional stirring at 0° C. for 30 min and rt for 2 h, the reaction mixture was concentrated to remove ethanol, then extracted with EtOAc (400 mL). The aqueous portion was further extracted with EtOAc (100 mL×3). The combined organic extracts were washed with water (80 mL×2), sat. aq. NaHCO₃ (80 mL), brine, dried over magnesium sulfate, filtered and concentrated under reduced pressure to give the title compound as a colorless oil. HPLC Ret. time: 2.62 min. LCMS MH+ (m/z) 188.33. ¹H NMR: (DMSO-d₆, 400 MHz): δ 7.65 (s, 1H), 7.62 (d, 1H), 7.38 (d, 1H), 5.49 (d, 1H), 4.59 (d, 1H), 2.70 (m, 2H), 1.13 (s, 3H), 0.83 (s, 3H).

Step C: 3-Azido-2,2-dimethyl-2,3-dihydro-1H-indene-5-carbonitrile

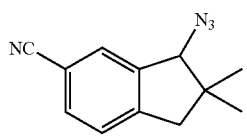

To a solution of Step B. 3-hydroxy-2,2-dimethyl-2,3-dihydro-1H-indene-5-carbonitrile (4.98 g, 0.027 mol) in toluene (60 mL) at 0° C. was added DPPA (8.6 mL, 0.040 mol) via syringe dropwise followed by DBU (6.0 mL, 0.040 mol) via syringe dropwise. After stirring at 0° C. for 10 min and rt for 30 min, the mixture was heated at 80° C. for 60 h, then cooled to rt and partitioned between EtOAc (400 mL)/water (100 mL). Resulting layers were separated and the organic layer was washed with water (100 mL), aq HCl (1N, 60 mL×2), water (100 mL), sat. aq. NaHCO₃ (80 mL), brine, dried over magnesium sulfate, filtered and concentrated under reduced pressure to give yellow oil as the crude product. Purification by flash chromatography on silica gel (120 g) eluting with EtOAc/hexane mixtures provided the title compound as a colorless oil (4.12 g, 73% yield). HPLC Ret. time: 3.37 min. LCMS MH+ (m/z) 213.3. ¹H NMR: (DMSO-d₆, 400 MHz): δ 7.86 (s, 1H), 7.76 (d, 1H), 7.49 (d, 1H), 4.74 (s, 1H), 2.80 (m, 2H), 1.13 (s, 3H), 1.06 (s, 3H).

Step D: (R)-3-Amino-2,2-dimethyl-2,3-dihydro-1H-indene-5-carbonitrile and (S)-3-amino-2,2-dimethyl-2,3-dihydro-1H-indene-5-carbonitrile

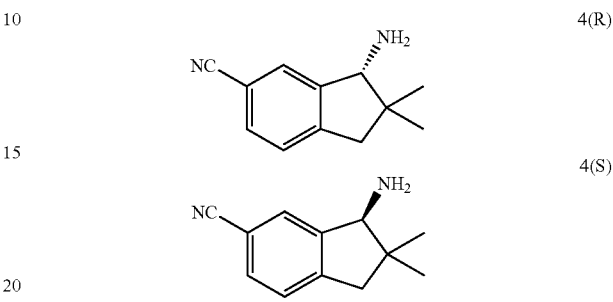

To a solution of Step C. 3-azido-2,2-dimethyl-2,3-dihydro-1H-indene-5-carbonitrile (4.12 g, 0.019 mol) in acetonitrile (63 mL) at 0° C. was added triphenylphosphine (6.10 g, 0.023 mol) in one portion followed by water (7.0 mL). The mixture was refluxed for 20 h, cooled to rt and concentrated to remove acetonitrile. Ether (300 mL) was added and the white solid was removed by filtration. The ether filtrate was extracted with aq HCl (1N, 100 mL×3). The combined acidic aqueous extracts were washed with ether (150 mL) and neutralized with aq NaOH (1.5 N, 300 mL) while cooling at 0° C. After saturating the aqueous portion with NaCl, the layer was extracted with ether (200 mL×3). The combined ether portions were washed with brine, dried over magnesium sulfate, filtered and concentrated under reduced pressure to give the product as a colorless oil (3.53 g, 97% yield). HPLC Ret. time: 1.31 min. LCMS MH+ (m/z) 187.34. ¹H NMR: (DMSO-d₆, 400 MHz): δ 7.86 (s, 1H), 7.76 (d, 1H), 7.49 (d, 1H), 4.74 (s, 1H), 2.80 (m, 2H), 1.13 (s, 3H), 1.06 (s, 3H).

Racemic mixture 4 was resolved by subcritical fluid chromatography (SFC) using a AD column and a 90:10 CO₂/MeOH mobile phase containing 0.1% DEA. Using these conditions, both enantiomers of 4 were obtained in >98% enantiomeric excess.

Step E: (R)—N-(6-Cyano-2,2-dimethyl-2,3-dihydro-1H-inden-1-yl)-5-hydroxy-1H-indole-2-carboxamide To a solution of 5-hydroxy-1H-indole-2-carboxylic acid (4.00 g, 0.023 mol) in DMF (40 mL) at rt was added HOBt (3.36 g, 0.025 mol) and EDAC (5.63 g, 0.029 mol). After stirring at rt for 15 min, Step D. (R)-3-amino-2,2-dimethyl-2,3-dihydro-1H-indene-5-carbonitrile (4.23 g, 0.023 mol) in DMF (20 mL) was added followed by DIPEA (4.43 mL, 0.027 mol). After stirring at rt for 3 h, the contents were poured into a mixture of aq. NH₄Cl (250 mL) and crushed ice (250 mL) with stirring. Solid was collected after 3 h and rinsed with water (50 mL×5) and dried to provide the crude product as cream colored solid. Purification by flash chromatography on silica gel using DCM/10% MeOH in DCM mixtures as the diluent provided the product as a cream-colored solid (7.74 g). The solid was taken up in EtOH (250 mL) and concentrated to remove ethanol, repeated. Then the solid was dissolved in EtOH (40 mL) and was added into cold water (600 mL) dropwise, stirred at 0° C. for 2 h and rt for 20 h. Solid was collected by filtration and rinsed with water and dried to give the final product (6.62 g, 85% yield) as cream-colored solid. HPLC Ret. time: 2.83 min. LCMS MH+ (m/z) 346.21. ¹H NMR: (DMSO-d$_6$, 400 MHz): δ 11.32 (br., 1H), 8.78 (s, 1H), 8.42 (d, J=9.23 Hz, 1H), 7.70 (d, J=7.70 Hz, 1H), 7.62 (s, 1H), 7.47 (d, J=7.70 Hz, 1H), 7.24 (d, J=8.74 Hz, 1H), 7.10 (d, J=1.57 Hz, 1H), 6.87 (d, J=2.20 Hz, 1H), 6.74 (dd, J=8.74 Hz, J=2.20 Hz, 1H), 5.38 (d, J=9.23 Hz, 1H), 2.88 (m, 2H), 1.22 (s, 3H), 0.94 (s, 3H).

Example 1A (S)—N-(6-Cyano-2,2-dimethyl-2,3-dihydro-1H-inden-1-yl)-5-hydroxy-1H-indole-2-carboxamide

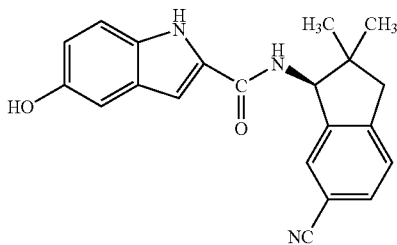

Following the procedure of Example 1 except substituting (S)-3-amino-2,2-dimethyl-2,3-dihydro-1H-indene-5-carbonitrile for the corresponding (R)-enantiomer, the title (S)-enantiomer was obtained as a white solid in 68% yield having an HPLC Ret. time of 2.85 min. and LCMS MH+ (m/z)= 346.37.

Example 2

(R)N-(6-Cyano-2,2-dimethyl-2,3-dihydro-1H-inden-1-yl)-5-chloro-1H-indole-2-carboxamide

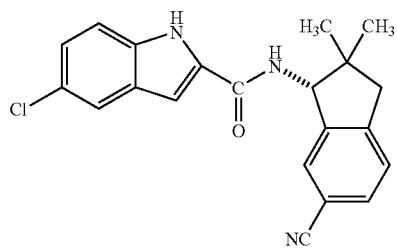

The title product was prepared as described in Example 1 using 5-chloro-1H-indole-2-carboxylic acid in place of 5-hydroxy-1H-indole-2-carboxylic acid in Step E. HPLC Ret. time: 3.64 min. LCMS MH+ (m/z) 364.97. ¹H NMR: (CDCl$_3$, 400 MHz): 9.36 (br s, 1H), 7.62 (d, 1H), 7.55-7.52 (m, 2H), 7.40 (d, 1H), 7.33 (d, 1H), 7.26 (dd, 1H), 6.85 (s, 1H), 6.26 (d, 1H), 5.52 (d, 1H), 2.88 (q, 2H), 1.36 (s, 3H), 1.04 (s, 3H).

Example 3

(R)-5-Chloro-N-(6-cyano-2,2-dimethyl-2,3-dihydro-1H-inden-1-yl)-1-methyl-1H-indole-2-carboxamide

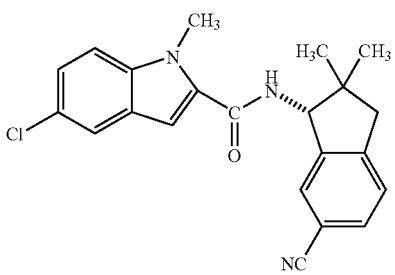

To a mixture of Example 2 N-(6-cyano-2,2-dimethyl-2,3-dihydro-1H-inden-1-yl)-5-chloro-1H-indole-2-carboxamide (30 mg, 0.083 mmol) and K$_2$CO$_3$ (34 mg, 2.48 mmol) in DMF (0.3 mL) was added methyl iodide (6 µL, 0.091 mmol) and the resulting mixture was stirred at rt for 16 h. Water (~5 mL) was added dropwise followed by stirring for an additional 30 min. The precipitated solid was collected by vacuum filtration, rinsed with additional water (~5 mL) and dried in vacuo to afford the title product as a white solid (26 mg). HPLC Ret. time: 3.79 min. LCMS MH+ (m/z) 378.30. ¹H NMR: (DMSO-d$_6$, 400 MHz): 8.72 (d, 1H), 7.71 (s, 1H), 7.68 (d, 1H), 7.65 (s, 1H), 7.58 (d, 1H), 7.44 (d, 1H), 7.26 (dd, 1H), 7.18 (s, 1H), 5.34 (d, 1H), 4.00 (s, 3H), 2.52-2.48 (m, 2H), 1.21 (s, 3H), 0.95 (s, 3H).

Example 4

(R)-5-Chloro-N-(6-cyano-2,2-dimethyl-2,3-dihydro-1H-inden-1-yl)-1-(2-(dimethylamino)ethyl)-1H-indole-2-carboxamide

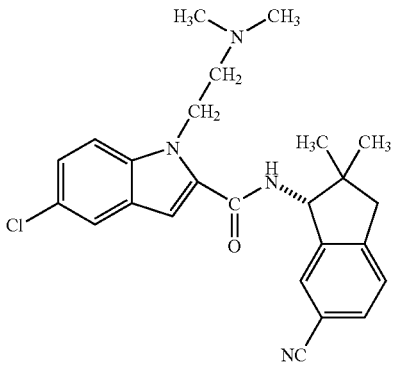

To a solution of N-(6-cyano-2,2-dimethyl-2,3-dihydro-1H-inden-1-yl)-5-chloro-1H-indole-2-carboxamide (30 mg, 0.083 mmol) in DMF (0.3 mL) at rt was added NaH (60% dispersion, 17 mg, 0.42 mmol). After stirring for 15 min, 2-chloro-N,N-dimethylethanamine hydrochloride (36 mg, 0.25 mmol) was added and the resulting mixture was heated at 65° C. for 4 h. After cooling to rt, the reaction mixture was subjected to purification by reverse-phase HPLC using MeOH/water mixtures with 0.1% TFA as the diluent. Fractions containing the major product were collected, combined and concentrated in vacuo to remove the MeOH. The resulting aqueous solution containing the product was made neutral by addition of sat. aq. NaHCO₃ and the product was extracted with EtOAc (3×10 mL). The combined extracts were washed with brine, dried over anhyd Na₂SO₄, filtered and concentrated in vacuo to afford an oil. The oil was redissolved in DCM/Et₂O (50/50, 2 mL) and reconcentrated to yield an oil which solidified under vacuum to afford the title compound in the form of a white solid (16 mg). HPLC Ret. time: 2.84 min. LCMS MH⁺ (m/z) 435.30. ¹H NMR: (MeOH-d₄, 400 MHz): 7.65 (d, 1H), 7.62-7.60 (m, 2H), 7.51 (d, 1H), 7.42 (d, 1H), 7.30 (dd, 1H), 7.12 (s, 1H), 5.45 (s, 1H), 4.80 (t, 2 H), 3.12 (br m, 2H), 2.93 (m, 2H), 2.59 (s, 6H), 1.32 (s, 3H), 1.07 (s, 3H).

Example 5

(R)-5-Chloro-N-(6-cyano-2,2-dimethyl-2,3-dihydro-1H-inden-1-yl)-1-(2-morpholinoethyl)-1H-indole-2-carboxamide

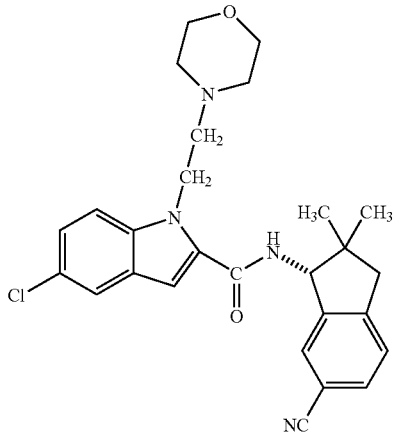

The title product in the form of a white solid was prepared as described in Example 4 using 4-(2-chloroethyl)morpholine hydrochloride in place of 2-chloro-N,N-dimethylethanamine hydrochloride. HPLC Ret. time: 2.81 min. LCMS MH⁺ (m/z) 477.30. ¹H NMR: (MeOH-d₄, 400 MHz): 7.64 (s, 1H), 7.62-7.60 (m, 2H), 7.53 (d, 1H), 7.42 (d, 1H), 7.30 (d, 1H), 7.11 (s, 1 H), 5.45 (s, 1 H), 4.80 (m, 2 H), 3.74 (br m, 4H), 2.92 (m, 2H), 2.80 (br m, 2H), 2.15 (s, 2H), 1.32, 1.07 (s, 3H).

Example 6

(R)—N-(6-Cyano-2,2-dimethyl-2,3-dihydro-1H-inden-1-yl)-1H-indole-2-carboxamide

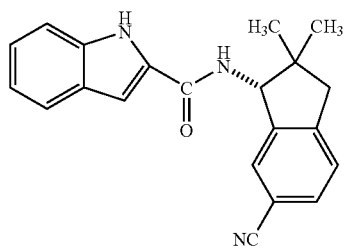

A mixture of 1H-indole-2-carboxylic acid (44.0 mg, 0.273 mmol), (R)-3-amino-2,2-dimethyl-2,3-dihydro-1H-indene-5-carbonitrile (34.0 mg, 0.182 mmol), BOP reagent (157 mg, 0.355 mmol), N-methylmorpholine (0.12 mL, 1.09 mmol) in DMF (0.5 mL) was stirred at 50° C. for 50 min. Dimethylamine (2.0 M in THF, 0.2 mL) was added to the mixture and the resulting mixture was stirred at 50° C. for 30 min. The desired title product (43.7 mg, 73% yield) was isolated as a white solid by prep. LCMS (M+H)⁺=330.33; HPLC. ¹H NMR (500 MHz, DMSO-d₆) δ: 11.6 (s, 1H), 8.53 (d, J=9.35 Hz, 1H), 7.70 (d, J=70 Hz, 1H), 7.60 (d, J=7.70 Hz, 1H), 7.62 (s, 1H) 7.46 (d, J=7.70 Hz, 1H), 7.44 (d, J=9.35 Hz, 1H), 7.29 (s, 1H), 7.18 (t, J=7.70 Hz, 1H), 7.03 (t, J=7.70 Hz, 1H), 5.38 (d, J=9.35 Hz, 1H), 2.86 (dd, J=22.5, 16.5 Hz, 2H), 1.21 (s, 3H), 0.94 (s, 3H). ¹³C NMR (125 MHz, DMSO-d₆) δ: 161.1, 148.2, 144.1, 136.2, 131.4, 131.0, 127.9, 126.7, 125.7, 123.0, 121.2, 119.4, 118.8, 111.9, 108.8, 103.2, 61.0, 39.4, 39.2, 39.1, 38.9, 27.1, 22.2.

Example 7

(R)—N-(6-Cyano-2,2-dimethyl-2,3-dihydro-1H-inden-1-yl)-5-fluoro-1H-indole-2-carboxamide

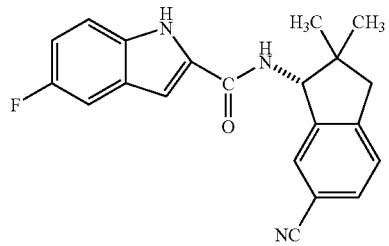

A mixture of 5-fluoro-1H-indole-2-carboxylic acid (56.0 mg, 0.312 mmol), (R)-3-amino-2,2-dimethyl-2,3-dihydro-1H-indene-5-carbonitrile (39.0 mg, 0.209 mmol), BOP reagent (180 mg, 0.407 mmol), N-methylmorpholine (0.13 mL, 1.18 mmol) in DMF (0.5 mL) was stirred at 50° C. for 2 hr. The desired title product (55.6 mg, 76% yield) was isolated as a white solid by prep. HPLC. LCMS (M+H)⁺=348.33. ¹H NMR (500 MHz, DMSO-d₆) δ: 11.7 (s, 1H), 8.58 (d, J=8.8 Hz, 1H), 7.70 (d, J=7.7 Hz, 1H), 7.62 (s, 1H), 7.46 (d, J=7.7 Hz, 1H), 7.44 (dd, J=8.8, 5.0 Hz, 1H), 7.39 (d, J=9.9 Hz, 1H), 7.28 (s, 1H), 7.04 (t, J=9.35 Hz, 1H), 5.37 (d, J=9.35 Hz, 1H), 2.87 (dd, J=22.0, 16.5 Hz, 2H), 1.21 (s, 3H), 0.94 (s, 3H).

Example 8

(R)—N-(6-Cyano-2,2-dimethyl-2,3-dihydro-1H-inden-1-yl)-5-nitro-1H-indole-2-carboxamide

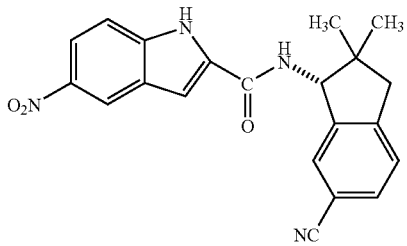

A mixture of 5-nitro-1H-indole-2-carboxylic acid (144 mg, 0.698 mmol), (R)-3-amino-2,2-dimethyl-2,3-dihydro-1H-indene-5-carbonitrile (110 mg, 0.591 mmol), BOP reagent (401 mg, 0.907 mmol), N-methylmorpholine (0.30 mL, 2.73 mmol) in DMF (2 mL) was stirred at rt for 16 hr. To the mixture was added 5% NaHCO$_3$ solution (35 mL) and the resulting mixture was stirred at rt for 15 min. The precipitating title product (250 mg) was collected as a beige solid by suction filtration and dried over Drierite® under vacuum. LCMS (M+H)$^+$=375.25. $^1$H NMR (500 MHz, DMSO-d$_6$) δ: 8.84 (d, J=9.3 Hz, 1H), 8.69 (s, 1H), 8.07 (d, J=8.8 Hz, 1H), 7.70 (d, J=8.2 Hz, 1H), 7.66 (s, 1H), 7.59 (d, J=11.0 Hz, 1H), 7.58 (s, 1H), 7.46 (d, J=7.7 Hz, 1H), 5.39 (d, J=9.3 Hz, 1H), 2.87 (dd, J=20.9, 16.5 Hz, 2H), 1.22 (s, 3H), 0.95 (s, 3H).

Example 9

(R)-5-Amino-N-(6-cyano-2,2-dimethyl-2,3-dihydro-1H-inden-1-yl)-1H-indole-2-carboxamide

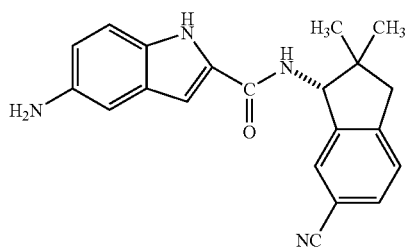

A mixture of (R)—N-(6-cyano-2,2-dimethyl-2,3-dihydro-1H-inden-1-yl)-5-nitro-1H-indole-2-carboxamide (200 mg, 0.534 mmol) (prepared as described in Example 8) and 10% Pd/C (80 mg) in 1:1 THF/MeOH (24 mL) was stirred at rt under H$_2$, provided a H$_2$ balloon, for 3 hr. The catalyst was removed by suction filtration, and the filtrate was concentrated under vacuum. The residue was diluted with ethyl acetate (50 mL), washed with brine (20 mL), and dried over anhydrous MgSO$_4$. It was concentrated under vacuum, and the residue was applied to ISCO (12 g silica gel, 40-55% ethyl acetate/hexane) to afford the desired title product (106 mg, 58% yield) as a pale yellow solid. LCMS (M+H)=345.38. $^1$H NMR (500 MHz, DMSO-d$_6$) δ: 11.1 (s, 1H), 8.33 (d, J=9.3 Hz, 1H), 7.69 (d, J=8.2 Hz, 1H), 7.59 (s, 1H), 7.45 (d, J=7.7 Hz, 1H), 7.14 (d, J=8.8 Hz, 1H), 6.98 (s, 1H), 6.68 (s, 1H), 6.61 (d, J=8.8 Hz, 1H), 5.35 (d, J=9.3 Hz), 4.60 (br. s, 2H), 2.86 (dd, J=23.6, 16.5 Hz, 2H), 1.20 (s, 3H), 0.93 (s, 3H).

Example 10

(R)—N-(6-Cyano-2,2-dimethyl-2,3-dihydro-1H-inden-1-yl)-5-(2-methoxyethylamino)-1H-indole-2-carboxamide

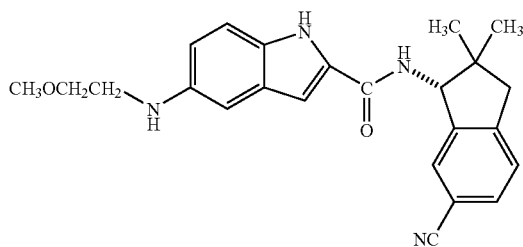

To a solution of (R)-5-amino-N-(6-cyano-2,2-dimethyl-2,3-dihydro-1H-inden-1-yl)-1H-indole-2-carboxamide (66.0 mg, 0.192 mmol) (prepared as described in Example 9) and methoxyacetaldehyde (containing 13% water, 18.0 mg, 0.211 mmol) in 1:1 THF/CH$_2$Cl$_2$ (4 mL) was added NaB(Oac)$_3$H at rt in one portion. The mixture was stirred at rt for 4 hr and the reaction was quenched with saturated with NaHCO$_3$ solution. The mixture was extracted with ethyl acetate (3×20 mL). The combined extract was washed with brine and dried over anhydrous MgSO$_4$. The desired product (27.1 mg, 35% yield) was isolated as a pale yellow solid by prep. HPLC. LCMS (M+H)$^+$=345.38. $^1$H NMR (500 MHz, DMSO-d$_6$) δ: 11.1 (s, 1H), 8.34 (d, J=9.3 Hz, 1H, 7.69 (d, J=8.2 Hz, 1H), 7.59 (s, 1H), 7.45 (d, J=7.7 Hz, 1H), 7.17 (d, J=8.8 Hz, 1H), 7.03 (s, 1H), 6.68 (d, J=8.2 Hz, 1H), 6.61 (s, 1H), 5.36 (d, J=9.3 Hz, 1H), 5.00 (t, J=5.8 Hz, 1H), 3.51 (t, J=6.0 Hz, 2H), 3.28 (s, 3H), 3.16 (dt, J=11.5, 6.0 Hz, 2H), 2.86 (dd, J=23.0, 16.5 Hz, 2H), 1.20 (s, 3H), 0.93 (s, 3H).

Example 11

(R)-Methyl-3-(5-chloro-1H-indole-2-carboxamido)-2,2-dimethyl-2,3-dihydro-1H-indene-5-carboxylate

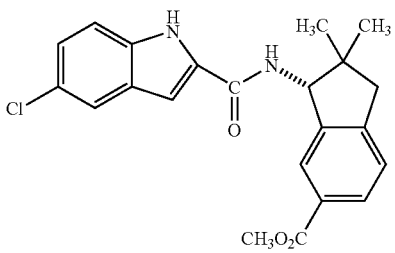

To a suspension of (R)-5-chloro-N-(6-cyano-2,2-dimethyl-2,3-dihydro-1H-inden-1-yl)-1H-indole-2-carboxamide (prepared as described in Examples 1 and 2) in MeOH (10 mL) at 0° C. was bubbled HCl (g) for 3 min. The mixture was then heated at 65° C. for 3 hr. The volatiles were removed under vacuum, and the residue was subjected to ISCO (12 g, silica gel, 10-20% ethyl acetate/hexane) to afford the desired title product (33.0 mg, 30% yield) as a white solid. LCMS (M+H)$^+$=397.20. $^1$H NMR (500 MHz, DMSO-d$_6$) δ: 7.91 (d, J=7.7 Hz, 1H), 7.87 (s, 1H), 7.59 (s, 1H), 7.43 (1H, J=8.8 Hz, 1H), 7.34 (d, J=8.2 Hz, 1H), 7.18 (d, J=8.2 Hz, 1H), 7.16 (s, 1H), 5.44 (s, 1H), 3.86 (s, 3H), 2.90 (dd, J=34.6, 16.5 Hz, 2H), 1.29 (s, 3H), 1.05 (s, 3H)

Compounds of formula I, including the compounds described in the examples hereof, have been tested in one or more of the assays described below and have shown activity as an agonist of CB2.

Filtration Binding Assay

Compound dilutions were carried out in duplicate in binding buffer [25 mM HEPES pH 7.4, 150 mM NaCl, 1 mM EDTA, 2 mM MgCl$_2$, 0.25% BSA, 1 mM leupeptin]. Mix binding buffer, membrane proteins (or CHO cells expressing hCB2 receptors) together. Dispense 75 ul of mixture into each well in 96 well plates. Add 1 ul of drug in DMSO, or DMSO alone into each well. 1:500-1000 dilute the hot ligand [$^3$H] CP55,940 (specific activity=120 Ci/mmol; PerkinElmer Life and Analytical Sciences) in binding buffer and add 25 ul per well with either 5 ug/well cell membrane or 50000 cells/well. After incubation at room temperature for 2 hours, transfer the binding reaction onto filtration plates (UniFilter CF/C filter plate presoaked with 0.3% polyethylenimine; PerkinElmer Life and Analytical Sciences) using Packard Cell Harvester. Wash the filter with quarter strength of PBS (1:4 dilution of regular PBS with H$_2$O) 8 times. Air dry the filter, add 40 ul MicroScint20 into each well, seal the top, and count with the TopCount. Bound radioactivity was analyzed for Ki using nonlinear regression analysis (Excel Xfit) with the Kd values for [3H]CP55,940 determined from saturation experiments.

GTPgS Binding Assay

Add 50 ul of reaction mixture containing 2 ug of CB2/CHO cell membrane proteins, 10 ul WGA-PVT beads (20 mg/ml), and 5 uM GDP in assay buffer (20 mM HEPES pH 7.4, 100 mM NaCl, 1 mM EDTA, 10 mM MgCl$_2$, 10 ug/ml saponin, 0.25% BSA, and 1 uM leupeptin) into each well in 96 well white plate (Corning 3693, VWR#29444-312). Add 1 ul of testing compound into test, 1 ul of DMSO into basal, 1 ul of 200 uM CP55,940 into 100% activation, 1 ul of 1 mM cold GTPγS into NSB wells, respectively. Dilute [$^{35}$S]GTPγS (1:12.5 pre-diluted 1 uCi/ul stock, NEG030H, NEN) 1:1350 in binding buffer and add 25 ul into each well (200 pM final). Incubate at RT for 90 min and spin the plate at 1000 rpm for 5 min before counting with TopCount for 1-2 min.

| | CB2 | | |
|---|---|---|---|
| Example No. | Structure | CB2 binding Ki (nM) | CB2 GTPgS EC50 (nM) |
| 1 | | 3 | 2.4 ± 0.55 |
| 1A | | 1588 | — |
| 2 | | 0.71 ± 0.18 | 2.2 ± 0.48 |
| 3 | | 7.6 ± 1.7 | 4.5 ± 1.2 |

-continued

| | CB2 | | |
|---|---|---|---|
| Example No. | Structure | CB2 binding Ki (nM) | CB2 GTPgS EC50 (nM) |
| 4 | (5-chloro-1-(2-(dimethylamino)ethyl)-1H-indole-2-carboxamide with 6-cyano-2,2-dimethyl-2,3-dihydro-1H-inden-1-yl, Chiral) | 60 ± 26 | 8.1 ± 2.2 |
| 5 | (5-chloro-1-(2-morpholinoethyl)-1H-indole-2-carboxamide with 6-cyano-2,2-dimethyl-2,3-dihydro-1H-inden-1-yl, Chiral) | 39 ± 14 | 7.8 ± 2.5 |
| 6 | (1H-indole-2-carboxamide with 6-cyano-2,2-dimethyl-2,3-dihydro-1H-inden-1-yl, Chiral) | 2.4 ± 1.1 | — |
| 7 | (5-fluoro-1H-indole-2-carboxamide with 6-cyano-2,2-dimethyl-2,3-dihydro-1H-inden-1-yl, Chiral) | 0.24 ± 0.12 | — |

-continued

| | CB2 | | | |
|---|---|---|---|---|
| Example No. | Structure | | CB2 binding Ki (nM) | CB2 GTPgS EC50 (nM) |
| 8 | [Chiral structure: 5-nitro-1H-indole-2-carboxamide linked to N-(2,2-dimethyl-6-cyano-2,3-dihydro-1H-inden-1-yl)] | | 4.2 ± 1.6 | — |
| 9 | [Chiral structure: 5-amino-1H-indole-2-carboxamide linked to N-(2,2-dimethyl-6-cyano-2,3-dihydro-1H-inden-1-yl)] | | 39 ± 14 | — |
| 10 | [Chiral structure: 5-((2-methoxyethyl)amino)-1H-indole-2-carboxamide linked to N-(2,2-dimethyl-6-cyano-2,3-dihydro-1H-inden-1-yl)] | | 50 ± 16 | — |
| 11 | [Chiral structure: 5-chloro-1H-indole-2-carboxamide linked to N-(2,2-dimethyl-6-(methoxycarbonyl)-2,3-dihydro-1H-inden-1-yl)] | | 35 ± 12 | — |

What is claimed is:

1. A compound having the formula

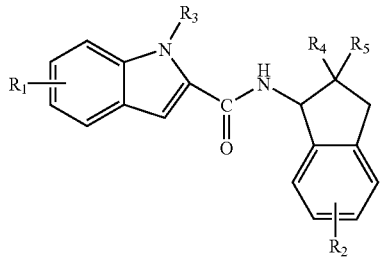

its enantiomers and diastereomers, or a pharmaceutically acceptable salt thereof, a prodrug thereof,
wherein
$R_1$ and $R_2$ are the same or different and are independently selected from the group consisting of
 a) hydrogen, hydroxyl, halogen, alkyl, alkoxy, alkoxyalkyl, cycloalkyl, aryloxy, nitro and cyano;
 b) an amino group, an amido group, carboxyl, alkoxycarbonyl and a urea group; and
 c) aryl, heteroaryl, and heterocyclo;
$R_3$ is hydrogen or alkyl; and
$R_4$ and $R_5$ are the same or different and are independently selected from the group consisting of hydrogen and alkyl.

2. The compound as defined in claim 1, its enantiomers and diastereomers, or a pharmaceutically acceptable salt thereof, a prodrug thereof, wherein the $R_1$ and/or $R_2$ amino group is $-NR_6R_7$;
the $R_1$ and/or $R_2$ amido group is

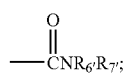

and
the $R_1$ and/or $R_2$ urea group is

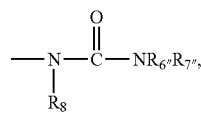

wherein $R_6$, $R_7$ and $R_6'$, $R_7'$ and $R_6''$ and $R_7''$ are the same or different and are independently selected from the groups consisting of hydrogen, alkyl, cycloalkyl, alkoxyalkyl, heteroaryl and heterocyclo; and
$R_8$ is hydrogen or alkyl.

3. The compound as defined in claim 1, its enantiomers and diastereomers, or a pharmaceutically acceptable salt thereof, a prodrug thereof, wherein $R_1$ is hydroxyl, halogen, hydrogen, nitro, amino, or alkoxyalkylamino.

4. The compound as defined in claim 3, its enantiomers and diastereomers, or a pharmaceutically acceptable salt thereof, a prodrug thereof, wherein $R_1$ is hydroxyl, chloro, hydrogen, fluoro, nitro, amino, or methoxyethylamino.

5. The compound as defined in claim 1, its enantiomers and diastereomers, or a pharmaceutically acceptable salt thereof, a prodrug thereof, wherein $R_2$ is cyano or alkoxycarbonyl.

6. The compound as defined in claim 1, its enantiomers and diastereomers, or a pharmaceutically acceptable salt thereof, a prodrug thereof, wherein $R_2$ is cyano or methoxycarbonyl.

7. The compound as defined in claim 1, its enantiomers and diastereomers, or a pharmaceutically acceptable salt thereof, a prodrug thereof, wherein $R_2$ is cyano.

8. The compound as defined in claim 1, its enantiomers and diastereomers, or a pharmaceutically acceptable salt thereof, a prodrug thereof, wherein $R_3$ is hydrogen, alkyl, dialkylaminoalkyl or heterocycloalkyl.

9. The compound as defined in claim 8, its enantiomers and diastereomers, or a pharmaceutically acceptable salt thereof, a prodrug thereof, wherein $R_3$ is hydrogen, methyl, dimethylaminoethyl, or morpholinylethyl.

10. The compound as defined in claim 1, its enantiomers and diastereomers, or a pharmaceutically acceptable salt thereof, a prodrug thereof, wherein $R_4$ and $R_5$ are the same or different and are independently selected from alkyl.

11. The compound as defined in claim 10, its enantiomers and diastereomers, or a pharmaceutically acceptable salt thereof, a prodrug thereof, wherein $R_4$ and $R_5$ are each methyl.

12. The compound as defined in claim 1, its enantiomers and diastereomers, or a pharmaceutically acceptable salt thereof, a prodrug thereof, wherein
$R_1$ is hydroxyl, halogen, hydrogen, nitro, amino or alkoxyalkylamino;
$R_2$ is cyano or alkoxycarbonyl;
$R_3$ is hydrogen, alkyl or heterocycloalkyl; and
$R_4$ and $R_5$ are the same or different and are alkyl.

13. The compound as defined in claim 12, its enantiomers and diastereomers, or a pharmaceutically acceptable salt thereof, a prodrug thereof, wherein
$R_1$ is hydroxyl, chloro, hydrogen, fluoro, nitro, amino or methoxyethylamino;
$R_2$ is cyano or methoxycarbonyl;
$R_3$ is hydrogen, methyl or morpholinylethyl; and
$R_4$ and $R_5$ are each methyl.

14. The compound as defined in claim 1 having the structure

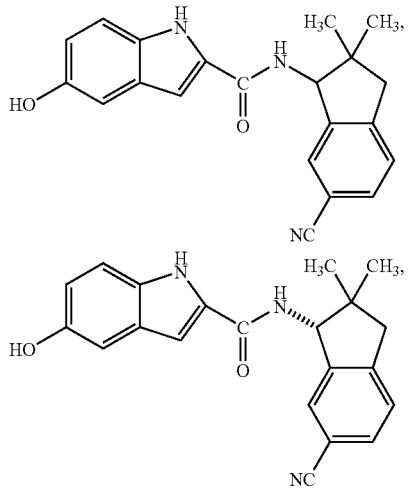

37
-continued
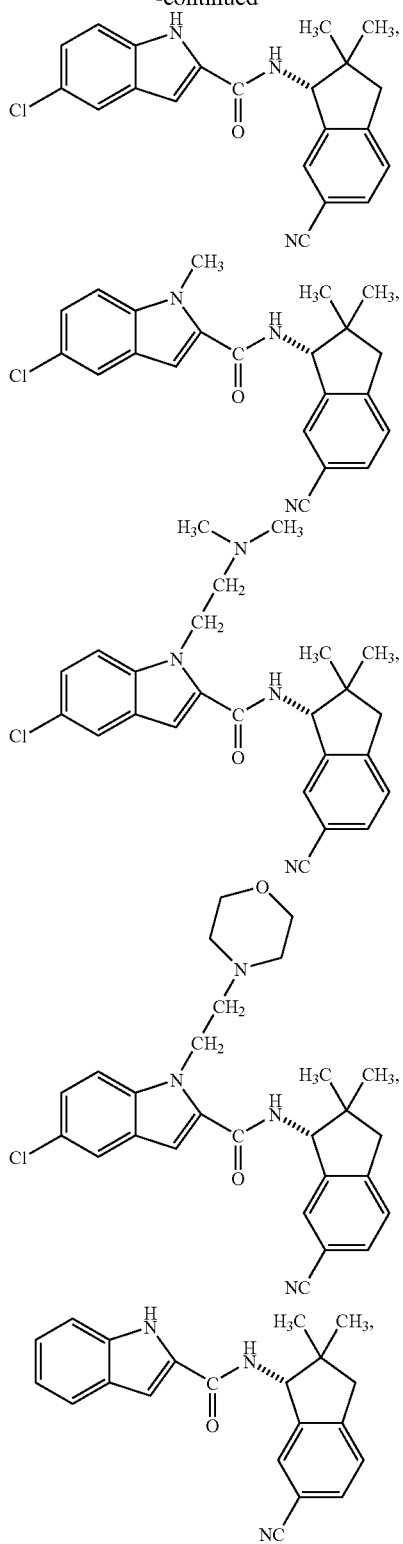
38
-continued
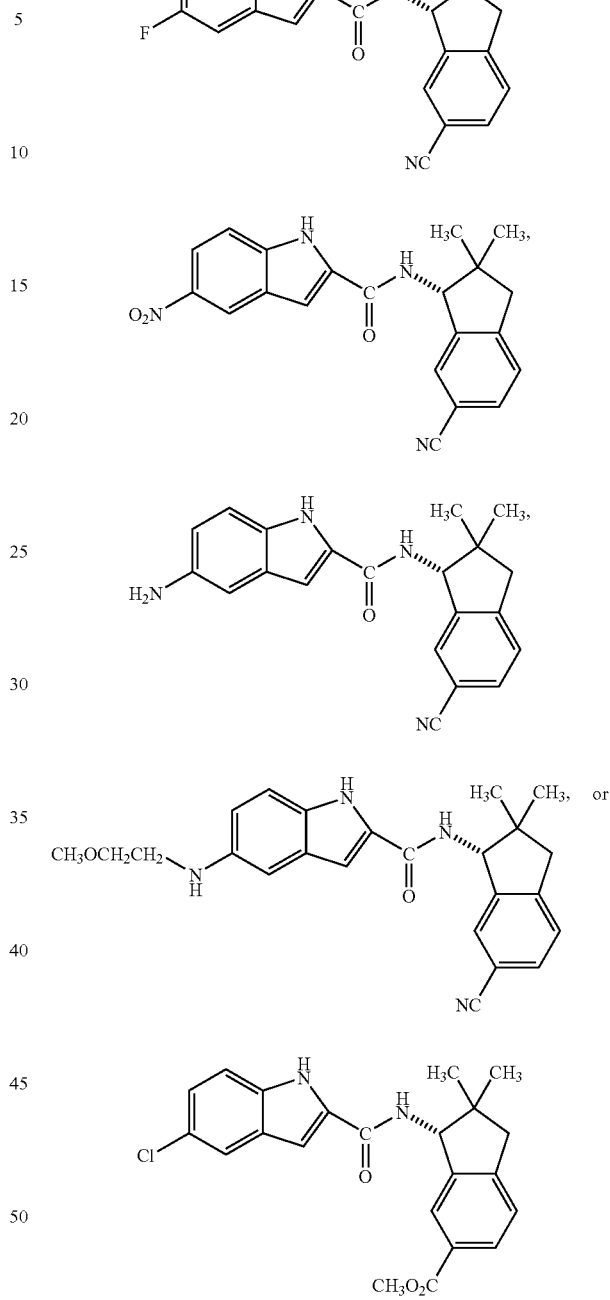
its enantiomers and diastereomers, or a pharmaceutically acceptable salt thereof, a prodrug thereof.
* * * * *

UNITED STATES PATENT AND TRADEMARK OFFICE
CERTIFICATE OF CORRECTION

| | | |
|---|---|---|
| PATENT NO. | : 7,943,658 B2 | Page 1 of 1 |
| APPLICATION NO. | : 12/177319 | |
| DATED | : May 17, 2011 | |
| INVENTOR(S) | : Chunjian Liu et al. | |

It is certified that error appears in the above-identified patent and that said Letters Patent is hereby corrected as shown below:

On the Title Page:

Item (56), References Cited, under OTHER PUBLICATIONS:

Column 2, Fuji, K. et al. reference, change "Pharmacal." to -- Pharmacol. --.
    The reference should read:
    -- Fuji, K. et al., "Novel Phosphodiesterase 4 Inhibitor T-440 Reverses and Prevents Human Bronchial Contraction Induced by Allergen", J. Pharmacol. Exp. Ther., 1998, 284(1): 162. --

Signed and Sealed this

Seventeenth Day of July, 2012

David J. Kappos
*Director of the United States Patent and Trademark Office*